(12) United States Patent
Navarro (10) Patent No.: US 11,883,400 B2
(45) Date of Patent: Jan. 30, 2024

(54) TREATMENT OF PORTAL HYPERTENSION AND CIRRHOSIS

(71) Applicant: Noorik Biopharmaceuticals AG, Basel (CH)

(72) Inventor: Iker Navarro, Riehen (CH)

(73) Assignee: Noorik Biopharmaceuticals AG, Basel (CH)

( * ) Notice: Subject to any disclaimer, the term of this patent is extended or adjusted under 35 U.S.C. 154(b) by 247 days.

(21) Appl. No.: 17/286,569

(22) PCT Filed: Oct. 21, 2019

(86) PCT No.: PCT/EP2019/025353
§ 371 (c)(1),
(2) Date: Apr. 19, 2021

(87) PCT Pub. No.: WO2020/094251
PCT Pub. Date: May 14, 2020

(65) Prior Publication Data
US 2021/0338667 A1 Nov. 4, 2021

(30) Foreign Application Priority Data

Oct. 19, 2018 (EP) ...................................... 18201419

(51) Int. Cl.
| | | |
|---|---|---|
| A61K 31/505 | (2006.01) | |
| A61P 1/16 | (2006.01) | |
| A61P 9/12 | (2006.01) | |
| A61K 9/00 | (2006.01) | |
| A61K 9/08 | (2006.01) | |
| A61K 9/20 | (2006.01) | |
| A61K 9/70 | (2006.01) | |

(52) U.S. Cl.
CPC ............ *A61K 31/505* (2013.01); *A61K 9/006* (2013.01); *A61K 9/0056* (2013.01); *A61K 9/08* (2013.01); *A61K 9/20* (2013.01); *A61K 9/7007* (2013.01); *A61P 1/16* (2018.01); *A61P 9/12* (2018.01)

(58) Field of Classification Search
CPC ...... A61K 31/505; A61K 9/0019; A61K 9/08; A61K 47/10; A61K 9/0056; A61K 9/006; A61K 9/20; A61K 9/7007; A61K 9/7084; A61K 31/00; A61K 31/513; A61K 9/00; A61P 1/16; A61P 9/00; A61P 9/12; A61P 13/12
See application file for complete search history.

(56) References Cited

U.S. PATENT DOCUMENTS

2014/0275094 A1* 9/2014 Gillies ............... A61K 31/4985
   514/249
2015/0125546 A1* 5/2015 Belardinelli ........... A61K 45/06
   514/274

FOREIGN PATENT DOCUMENTS

| WO | 2017/158199 | 9/2017 | | |
|---|---|---|---|---|
| WO | WO2017/158199 A1 | * | 9/2017 | ............. A61K 31/00 |
| WO | WO2017/158199 A1 | * | 9/2017 | ............. A61K 31/00 |

OTHER PUBLICATIONS

Baffy, "Origins of Portal Hypertension in Nonalcoholic Fatty Liver Disease", Digestive Diseases and Sciences, vol. 63, No. 3, pp. 563-576 (2018).
Moreno et al., "Portal Blood Flow in Cirrhosis of the Liver", The Journal of Clinical Investigation, vol. 46, No. 3: 436-445 (1967).
Bosch et al., "The clinical use of HVPG measurements in chronic liver disease", Nature Reviews, Gastroenterology & Hepatology, vol. 6, No. 10: pp. 573-582 (2009).
Moore, "Endothelin and vascular function in liver disease", Gut, vol. 53, No. 2: pp. 159-161 (2004).
Moore et al., "Plasma Endothelin Immunoreactivity in Liver Disease and the Hepatorenal Syndrome", The New England Journal of Medicine, vol. 327, No. 25: pp. 1774-1778 (Dec. 1992).
Okamoto et al., "Antifibrotic effects of ambrisentan, an endothelin-A receptor antagonist, in a non-alcoholic steatohepatitis mouse model", World J. Hepatology, vol. 8, No. 22: pp. 933-941 (2016).
Pitts, "Endothelin receptor antagonism in portal hypertension", Expert Opin. Investig. Drugs, vol. 18, No. 2: pp. 135-142 (2009).
Tripathi et al., "Endothelin-1 contributes to maintenance of systemic but not portal haemodynamics in patients With early cirrhosis: a randomized controlled trial", Gut, vol. 55, No. 9: pp. 1290-1295 (2006).
Zipprich et al., "Selective Endothelin-A-Blocker decrease portal pressure in patients With cirrhosis. A feasibility study combining the local intraarterial and systemic administration", Z. Gastroenterol, vol. 54, No. 12: pp. 1342-1404 (Dec. 2016).
Halank et al., "Ambrisentan improves exercise capacity and symptoms in patients with portopulmonary hypertension", Z. Gastroenterol, vol. 49, No. 9: pp. 1258-1262 (2011).
Savale et al., "Efficacy, safety and pharmacokinetics of bosentan in portopulmonary hypertension", Eur. Respir. J., vol. 41, No. 1, pp. 96-103 (2013).
Hoeper et al., "Experience with inhaled iloprost and bosentan in portopulmonary hypertension", Eur. Respir. J., vol. 30, No. 6: pp. 1096-1102 (Dec. 2007).
Kahler et al., "Successful treatment of portopulmonary hypertension with the selective endothelin receptor antagonist Sitaxentan", Wien. Klin. Wochenschr., vol. 123, No. 7-8, pp. 248-252 (Apr. 2011).
Muraoka et al., "Secure Combination Therapy With Low-Dose Bosentan and Ambrisentan to Treat Portopulrnonary Hypertension Minimizing Each Adverse Effect", In. Heart J., vol. 56, No. 4: pp. 471-473 (2015).

(Continued)

*Primary Examiner* — Audrea B Coniglio
*Assistant Examiner* — Audrea Buckley
(74) *Attorney, Agent, or Firm* — Wenderoth, Lind & Ponack, L.L.P.

(57) ABSTRACT

Methods and formulations are provided for the treatment and prevention of portal hypertension.

2 Claims, 1 Drawing Sheet

(56) References Cited

OTHER PUBLICATIONS

Yamashita et al., "Hemodynamic effects of ambrisentan-tadalafil combination therapy on progressive portopulmonary hypertension", World J. Hepatology, vol. 6, No. 11: pp. 825-829 (Nov. 2014).
Hinterhuber et al., "Endothelin-receptor antagonist treatment of portopulmonary hypertension", Clin. Gastroenterol. Hepatol., vol. 2, No. 11: pp. 1039-1042 (2004).
Sitbon et al., "Macitentan for the treatment of portopulmonary hypertension (PORTICO): a multicentre, randomised, double-blind, placebo-controlled, phase 4 trial", Lancet Respir. Med., vol. 7, No. 7: pp. 594-604 (2019).
Cartin-Ceba et al., Safety and efficacy of ambrisentan for the therapy of portopulmonary hypertension (POPH), Hepatology, vol. 50, No. 4: pp. 348A-3494 (2009).
Cartin-Ceba et al., "Safety and efficacy of ambrisentan for the treatment of portopulmonary hypertension", Chest, vol. 139, No. 1: pp. 109-114 (Jan. 2011).
Cartin-Ceba et. al., "Portopulmonary hypertension", Clin. Liver Dis., vol. 18, No. 2: pp. 421-438 (2014).
International Search Report dated Jul. 10, 2020 in international application no. PCT/EP2019/025353.
Assessment Report for Volibris, European Medicines Agency, pp. 1-44 (Apr. 1, 2008).
Portal Hypertension, Jul. 31, 2023, https://my.clevelandclinic.org/health/diseases/4912-portal-hypertension, pp. 1-12.
Pulmonary Hypertension (PH), Jul. 31, 2023, https://my.clevelandclinic.org/health/diseases/6530-pulm0nary-hypertension-ph, pp. 1-23.
Simonneau, G., et al., "Updated Clinical Classification of Pulmonary Hypertension", Journal of the American College of Cardiology, 2009, vol. 54, No. 1, Suppl S, pp. S43-S54.
Ryan, J. J., et al., "The WHO Classification of pulmonary hypertension: A case-based imaging compendium", Pulmonary Circulation, 2012, vol. 2, No. 1, pp. 107-121.
Simonneau, G., et al., "Clinical Classification of Pulmonary Hypertension", Journal of the American College of Cardiology, 2004, vol. 43, No. 12, Suppl S, pp. 5S-12S.
Summary of Product Characteristics (SMPC) from the European Medicines Agency for Volibris (ambrisentan), pp. 1-46 (2023).
United States Package Insert (USPI) for Letairis (ambrisentan), pp. 1-25 (2018).

* cited by examiner

TREATMENT OF PORTAL HYPERTENSION AND CIRRHOSIS

CROSS-REFERENCE TO RELATED APPLICATIONS

Not Applicable

FIELD

This invention relates to the treatment and prevention of Portal Hypertension and its complications, in particular to Portal Hypertension associated with cirrhosis and to related therapeutic and prophylactic formulations.

BACKGROUND

Portal hypertension (also referred to as "increased portal pressure") is an abnormal increase in pressure of the portal venous system, which drains blood from the intestine, pancreas and spleen into the liver. Portal hypertension is of importance as it is the underlying abnormality leading to the major complications of cirrhosis, which account for most of the morbidity and mortality in patient with cirrhosis. These major complications include ascites and its complications (e.g. spontaneous bacterial peritonitis, refractory ascites, hepatorenal syndrome, dilutional hyponatremia), upper gastrointestinal bleeding from gastroesophageal varices, pulmonary arterial hypertension (referred to as Portopulmonary Hypertension), splenomegaly and thrombocytopenia, jaundice and hepatic encephalopathy, among others.

Cirrhosis resulting from chronic liver disease is by far the most common cause of portal hypertension. Causes of cirrhosis include chronic infections or infestations of the liver (Hepatitis B, Hepatitis C, Schistosomiasis, others), alcoholic liver disease, non-alcoholic fatty liver disease (including Non-Alcoholic Fatty Liver Disease [NAFLD] and Non-Alcoholic Steatohepatitis [NASH]), autoimmune hepatitis, primary biliary cholangitis (also referred to as primary biliary cirrhosis), polycystic disease, genetic diseases, inborn errors of metabolism, metabolic diseases and others. However, portal hypertension may also be observed in in the absence of cirrhosis or fibrosis. For example, subjects with NAFLD and NASH may develop an increase in portal pressure in the early stages of the disease and in the absence of significant fibrosis, a finding that has also been observed in animal studies [1].

Fibrosis of the liver is a protracted process observed in patients with chronic liver disease and which may progress to cirrhosis. During the process of fibrosis, deposition of extracellular matrix components such as collagen results in tissue scarring of the liver. Once additional intra-hepatic structural abnormalities are observed (i.e. septal formation and other vascular structural abnormalities), the condition is referred to as cirrhosis. Functional abnormalities of the liver and an abnormal vascular organization lead over time to portal hypertension. In some patients, portal hypertension and its complications may be observed in earlier stages of chronic liver disease and in the absence of significant fibrosis or overt cirrhosis, for example in patients with NAFLD and NASH.

As with any other vessel, pressure across the portal venous system is proportional to blood flow and the resistance to blood flow (Ohm's law, where $\Delta P = F \times R$). In liver fibrosis and cirrhosis, portal hypertension results from an increased intra-hepatic resistance to portal flow and, frequently, a concurrent increase in blood return to the portal venous system. The intra-hepatic resistance to portal flow is the result of the loss of normal liver tissue architecture through extensive fibrosis and hepatic sinusoidal vasoconstriction, the latter mediated in part by vasoactive peptides such as endothelin. Increased portal flow results from a higher blood flow return from the mesenteric and splenic veins and mediated by splanchnic vasodilation. Under normal conditions, it is estimated that about 75% of blood flow through the liver is delivered through the portal venous system, the rest delivered through the hepatic artery. In subjects with liver fibrosis and cirrhosis, a progressive and significant reduction in hepatic blood flow is observed [2]. In some patients with advanced disease, there is no portal flow at all, or portal flow may be retrograde from the liver into the portal venous system. In subjects with significant portal hypertension, the blood supply to the liver is predominantly maintained by the hepatic arterial circulation. In the absence of cirrhosis and significant fibrosis, portal pressure may also increase in patients with NAFLD and NASH, as a result of the activation of vasoconstrictive systems in the liver vascular system, such as the activation of the endothelin system, resulting in sinusoidal vasoconstriction and increasing intra-hepatic resistance to portal blood flow.

Current therapeutic modalities for portal hypertension lower portal pressure by reducing portal blood flow, and not by reducing intra-hepatic resistance. A reduction in portal blood flow is achieved by reducing the return of blood to the liver through the portal venous system (e.g. beta-blockers, midodrine, somatostatin, terlipressin), reducing cardiac output (e.g. beta-blockers) or by shunting portal blood flow to the systemic circulation and partially bypassing the intra-hepatic circulation (e.g. Transjugular Intrahepatic Portosystemic Shunt [TIPS], where a physical shunt is created between the portal vein and a hepatic vein). The benefit of the current interventions for portal hypertension is limited as they do not address the root cause of portal hypertension, that is the increase in intra-hepatic vascular resistance. As such, current therapies effectively reduce hepatic blood flow and oxygen delivery to the liver is compromised. As ischemia is a significant contributor to organ fibrosis, portal hypertension can be considered both a result and a promoter of liver fibrosis and cirrhosis, and current treatment modalities for portal hypertension may aggravate liver ischemia and promote fibrosis. Furthermore, not all subjects benefit from the current treatment modalities and not all subjects tolerate them. To date, no therapeutic intervention is available that directly targets intra-hepatic resistance to portal flow.

Given that its direct measurement is technically difficult, the current gold standard for estimating portal pressure is the measurement of the Hepatic Venous Pressure Gradient (HVPG) [3], which provides an accurate estimate of pressure in the portal venous system. HVPG has been shown to correlate well with portal venous pressure, is reproducible, safe and has become the preferred investigation to provide information on the disease stage and assess the response to therapy of cirrhosis or its complications. Higher HVPG values in patients with cirrhosis have been shown to strongly predict survival, as well as the onset and severity of the major complications of cirrhosis. Conversely, a reduction in HVPG following therapeutic interventions (e.g. beta-blockers, midodrine, terlipressin and somatostatin analogues, and TIPS) has been shown to predict a reduced incidence and severity of the complications of cirrhosis and overall mortality. As such, HVPG is considered a good surrogate marker of disease severity and predictor of morbidity and mortality.

Bosch et al. [3] provide an overview of portal hypertension and the importance of HVPG as a marker of prognosis and therapeutic response.

Endothelin, a family of endogenous peptides, has complex vascular effects in humans. Endothelin has two receptors in humans: the ETA receptor which mediates vasoconstriction when stimulated by endothelin, and the ETB receptor which mediates vasodilation when stimulated by endothelin. In the kidney, the ETB receptor has the additional effect of promoting the clearance of water. The ETB receptor is also a clearance receptor of endothelin.

Endothelin is known to participate in the vascular and inflammatory mechanisms of some forms of cirrhosis [4], [5]. In particular, endothelin mediates the intra-hepatic increase in vascular tone which results in an increase in portal pressure [4]. Endothelin receptor antagonists have been shown to revert the effects of endothelin in animal models of cirrhosis and lower portal pressure by blocking the effects of endothelin on the ETA receptor. In animals, chronic endothelin antagonism has also been shown to prevent the progression of liver fibrosis [6]. Pitts [7] provides an overview of animal studies describing the role of endothelin receptor antagonism in preventing and reverting changes in portal pressure, liver fibrosis and cirrhosis. In humans, several studies have recently explored the benefit of endothelin receptor antagonists in reducing portal pressure in patients with cirrhosis. Tripathi et al. [8] assessed the systemic and portal hemodynamic effects of selective ETA (BQ-123) and selective ETB (BQ-788) receptor antagonism in subjects with cirrhosis. Endothelin was shown to contribute to the maintenance of systemic and pulmonary haemodynamics through the ETA receptor. However, in this study endothelin receptor antagonism (ETA selective or ETB selective) did not show any acute reduction on portal pressure as assessed by HVPG in patients with early cirrhosis. Conversely, Zipprich et al. [9] have reported the acute effects of BQ-123 and ambrisentan in patients with cirrhosis. In the initial study, BQ-123 was administered through the hepatic artery. In the second study, ambrisentan was administered orally at doses of 5 mg and 10 mg. Both BQ-123, and ambrisentan when given at 5 mg and 10 mg reduced portal pressure by 18%, 4.8% and 7%, respectively and as determined by HVPG. However, in this study the effect of BQ-123 (a less potent selective ETA receptor antagonist than ambrisentan and with a shorter half-life) showed a more marked reduction in portal pressure than ambrisentan. The administration of ambrisentan at the higher dose (10 mg) showed a larger reduction in portal pressure than the lower dose (5 mg) supporting a dose-response effect, albeit both reductions in HVPG were less than that achieved by BQ-123. Furthermore, BQ-123 induced a significant increase in hepatic artery blood flow. Given that BQ-123 is a less potent ETA antagonist than ambrisentan, it is difficult to explain the inferior results obtained with higher doses of ambrisentan when compared to the results in HVPG and arterial blood flow observed with BQ-123.

A less common complication of cirrhosis is the coexistence of portal hypertension and pulmonary arterial hypertension, a condition referred to as portopulmonary hypertension. Several case reports and series have been published where selective and non-selective endothelin receptor antagonists have been used to treat patients with portopulmonary hypertension ([10]-[15] among others). However, these series and case reports have not reported the effect of endothelin receptor antagonism on portal pressure, to the exception of Hinterhuber et al. [16], who reported a case of portopulmonary hypertension where HVPG was also measured. In this patient, treatment with bosentan (a non-selective endothelin receptor antagonist) resulted in a decrease of pulmonary pressure and portal pressure as measured by HVPG. Several clinical studies are ongoing evaluating the benefit of endothelin receptor antagonists in patients with portopulmonary hypertension, specifically ambrisentan and macitentan (studies NCT01224210 and NCT02382016 in Clinicaltrials.gov). The current study of ambrisentan (NCT01224210) in portopulmonary hypertension is exploring the benefit of the 5 and 10 mg once daily doses and escalating the dose to the highest dose possible (10 mg). Results from the clinical study of macitentan have indicated that macitentan had no effect on a the clinical endpoint of 6-minute walking distance in patients with portopulmonary hypertension, as well as not showing a significant difference in portal pressure as determined by HVPG [17]. Cartin-Ceba et al., have reported a beneficial effect of ambrisentan in treating patients with portopulmonary hypertension, but no mention of an improvement in portal pressure has been described [18]-[20].

A significant interest in the role of endothelin receptor antagonists in cirrhosis has translated into several lines of research, both in animals and in humans, with the goal of evaluating the therapeutic utility of these agents. However, to date no endothelin receptor antagonist is available for the treatment of portal hypertension, the major complications of cirrhosis or the progression of liver fibrosis to cirrhosis. Although the current state of the art supports a role for endothelin receptor antagonism, the available information is limited, and the results in humans have been inconsistent and contradictory.

SUMMARY

The inventors have found that portal hypertension, in particular portal hypertension associated with cirrhosis, can be prevented and treated by administering selective ETA antagonists in amounts that block the endothelin receptor subtype A (ETA) while not significantly blocking the endothelin receptor subtype B (ETB).

The inventors have further found that the major complications of cirrhosis (e.g. ascites, variceal bleeding, hepatic encephalopathy and jaundice), can be prevented and treated by reducing portal pressure through the administration of selective ETA antagonists in amounts that block the endothelin receptor subtype A (ETA) while not significantly blocking the endothelin receptor subtype B (ETB).

The inventors have further found that portopulmonary hypertension, can be prevented and treated by administering selective ETA antagonists in amounts that block the endothelin receptor subtype A (ETA) while not significantly blocking the endothelin receptor subtype B (ETB).

The inventors have further found that the progression of liver fibrosis and cirrhosis can be prevented by the administration of selective ETA antagonists in amounts that block the endothelin receptor subtype A (ETA) while not significantly blocking the endothelin receptor subtype B (ETB).

The inventors have further found that the progression of Non-Alcoholic Steatohepatitis (NASH) can be prevented by the administration of selective ETA antagonists in amounts that block the endothelin receptor subtype A (ETA) while not significantly blocking the endothelin receptor subtype B (ETB).

The inventors have further found that selective ETA antagonists interact with and antagonize the ETB receptor when administered at doses approved for the treatment of other conditions such as pulmonary arterial hypertension. In this regard, several endothelin receptor antagonists are approved for oral administration to treat pulmonary arterial hypertension, such as ambrisentan and other compounds discussed below. Some of these, including ambrisentan, are considered ETA selective antagonists. However, their systemic administration in approved dosage forms, notwithstanding their selectivity for the ETA receptor, results in plasma levels that are not ETA receptor selective and therefore are ineffective in preventing and treating portal hypertension.

In particular, the formulations and methods of the present invention are intended to treat or prevent conditions where portal pressure is increased such as portal hypertension, in particular portal hypertension associated with cirrhosis, ascites, variceal bleeding, hepatic encephalopathy, jaundice, portopulmonary hypertension, Non-Alcoholic Steatohepatitis (NASH) and the progression of liver fibrosis and cirrhosis.

Achieving the benefits of the present invention requires new and improved formulations for selective ETA antagonists and new methods for their therapeutic use. Accordingly, one objective of the present invention is to provide novel formulations of ETA antagonists and to provide a new medical use of ETA antagonists.

DESCRIPTION OF INVENTION AND EMBODIMENTS

The present invention relates to a finding that maintaining relatively low blood plasma concentrations of selective ETA antagonists, such as ambrisentan in a preferred embodiment, is effective to treat or prevent portal hypertension, in particular portal hypertension associated with cirrhosis. The plasma concentrations of such ETA antagonists are preferably monitored because even selective ETA antagonists may partially antagonize ETB when the ETA are saturated with the antagonist. Because blocking the ETB receptor prevents vasodilation and the reduction of portal hypertension, the clinical benefit provided by the ETA antagonist decreases or even disappears entirely if the effects of endothelin on the ETB receptors are also significantly antagonized.

The present invention and its embodiments are discussed in greater detail below.

Definitions

"Amount effective to reduce portal pressure" means that the amount of the administered compound will antagonize or block intra-hepatic, sinusoidal, arterial and/or portal vein ETA receptors, and other cellular components of the liver sufficiently to reduce portal pressure or prevent and treat the major complications of increased portal pressure or portal hypertension, such as ascites, formation of gastroesophageal varices, variceal bleeding, hepatic encephalopathy, jaundice, portopulmonary hypertension as well as the progression of liver fibrosis. The "amount effective" or "effective amount" refer to an amount effective, at dosages and for periods of time necessary, to achieve the desired therapeutic or prophylactic result. Such effective amounts can be expressed in daily doses of the endothelin receptor antagonist and/or in the blood concentrations of the endothelin receptor antagonist, as is discussed herein. For increased portal pressure, an effective amount is determined based on the amount necessary to achieve a decrease in portal pressure as determined by HVPG or any other suitable method over a period of time. For portal hypertension, an effective amount is determined based on the amount necessary to achieve a decrease in portal pressure as determined by HVPG or any other suitable method to determine portal pressure and over a period of time. For portopulmonary hypertension, an effective amount is determined based on the amount necessary to achieve a decrease in pulmonary pressure, a decrease in pulmonary capillary wedge pressure, a decrease in pulmonary vascular resistance, and/or an increase in 6-minute walking distance over a period of time. For ascites, an effective amount is determined based on the amount necessary to achieve a decrease in the severity or frequency of ascites, a decrease in the severity or frequency of weight gain, a decrease in the frequency of paracentesis, a decrease in the volume of ascitic fluid obtained at the time of paracentesis and/or a decrease in the dose and frequency of diuretic drug use over a period of time. For variceal bleeding, an effective amount is determined based on the amount necessary to achieve a decrease in the incidence and size of gastroesophageal varices as determined by endoscopy or a decrease in the incidence and frequency of gastroesophageal bleeding events over a period of time. For jaundice, an effective amount is determined based on the amount necessary to achieve a decrease in the incidence and severity of icteric episodes and/or a decrease in levels of bilirubin in blood over a period of time. For hepatic encephalopathy, an effective amount is determined based on the amount necessary to achieve a decrease in frequency and severity of hepatic encephalopathy events and/or a decrease in the grade of neuropsychiatric impairment as determined by an accepted clinical scale (e.g. West Haven Criteria) over a period of time. For progression of liver fibrosis and cirrhosis, an effective amount is determined based on the amount necessary to prevent an increase in portal pressure, the progression in the histological stage of liver injury according to well accepted scales (e.g. International Association for the Study of the Liver scale [IASL], Metavir Scale, Batts-Ludwig score, Ishak grade, Knodell score among others) and/or any other suitable method used to assess the progression of cirrhosis over a period of time such as by laboratory or imaging (e.g. ultrasonographic methods such as transient or shear-wave elastography) investigations or by clinical evaluation (e.g. Child-Pugh score). For the progression of NASH, an effective amount is determined based on the amount necessary to prevent an increase in portal pressure, the progression in the histological stage of liver injury according to well accepted scales (e.g. International Association for the Study of the Liver scale [IASL], Metavir Scale, Batts-Ludwig score, Ishak grade, Knodell score among others) and/or any other suitable method used to assess the progression of NASH over a period of time such as by laboratory or imaging (e.g. ultrasonographic methods such as transient or shear-wave elastography) investigations or by clinical evaluation (e.g. Child-Pugh score).

"Ascites" refers to the abnormal accumulation of fluid in the peritoneal cavity and causing abdominal swelling when the accumulation of fluid is significant.

"Cirrhosis" refers to the extensive fibrosis of the liver and loss of normal liver tissue architecture. Histologically, it is characterized by the development of regenerative nodules surrounded by fibrous bands in response to chronic liver injury, that leads to portal hypertension and end stage liver disease.

"Does not significantly antagonize endothelin receptor type B" means that the administered compound does not antagonize ETB at all or to such an extent that the vasodilatory effect of the ETA antagonism is not compromised or adverse renal effects, such as fluid retention and which are secondary to an antagonism of the ETB receptor, are not observed in a patient. When the ETB is significantly antagonized, the reduction in portal pressure caused by antagonizing ETA is reduced, not observed or even counteracted completely. Such antagonism of ETB can be established by determining the concentration of endothelin in the blood. When ETB is not blocked by the antagonist, the endothelin concentration will be similar to before treatment. When ETB is fully antagonized, the endothelin concentration after treatment with the antagonist will be higher than the level measured before treatment. With preferential ETA blockade, the endothelin concentration in the blood is at most 150% of the endothelin concentration before treatment, more preferably at most 130%, even more preferably at most 120%, and even more preferably at most 110% of the endothelin concentration before treatment. Most preferably, the endothelin concentration is the same in the blood after treatment with the selective ETA antagonist. When significantly antagonized in a patient, the incidence and severity of adverse renal effects such as weight gain, retention of fluid, formation of ascites, and/or pulmonary edema are increased.

"Gastroesophageal varices" or "varices" refers to dilated sub-mucosal veins in the lower third of the esophagus or stomach and the result of increased pressure in the portal venous system.

"Gastroesophageal bleeding" or "variceal bleeding" refers to the bleeding of varices formed in the esophagus and/or stomach as a result of portal hypertension.

"Hepatic encephalopathy" refers to a spectrum of neuropsychiatric abnormalities, such as personality changes, intellectual impairment, and/or a depressed level of consciousness observed in patients with liver dysfunction, after exclusion of brain disease.

"Hepatic Venous Pressure Gradient" also referred to as HVPG, is an invasive assessment of the difference between the wedged and free blood pressures obtained by catheterization of a main hepatic vein, and the difference, reported in mmHg, is an appropriate estimate of the pressure in the portal venous system.

"Improved portal pressure" (and variations thereof such as "improvement in portal pressure") means that a subject who receives the compounds and formulations according to the present invention shows a reduction in portal pressure and a reduction in the incidence or severity of the major complications of increased portal pressure. Such improvement may be associated with beneficial changes, including, for example, decreased incidence and severity of ascites, a decreased incidence and severity of peripheral edema, reduction in the size of gastroesophageal varices, a reduced incidence of upper gastrointestinal bleeding, a reduction in the size of the spleen, an increase in circulating blood platelets, an improvement in hepatic encephalopathy, an increase in blood protein concentration, a decrease in blood liver enzymes, a decrease in serum bilirubin concentrations, or a normalization of coagulation times. For example, patients treated according to the present invention may show a reduction in portal pressure as determined by HVPG of 10%, preferably 20% or a reduction of portal pressure as determined by HVPG to less than 12 mmHg, preferably to less than 10 mmHg, and most preferably to 5 mmHg or less.

"Individual" or "subject" or "patient" is a mammal. Mammals include, but are not limited to, domesticated animals (for example, cows, sheep, cats, dogs, and horses), primates (for example, humans and non-human primates such as monkeys), rabbits, and rodents (for example, mice and rats). In preferred embodiments, the individual or subject is a human being.

"Jaundice" refers to yellowing of the skin or sclera of the eyes, arising from excess of the pigment bilirubin and typically caused by obstruction of the bile duct, by liver disease, or by excessive breakdown of red blood cells.

"Liquid composition for parenteral administration" or "liquid formulation for parenteral administration" refers to a preparation which is suitable for intravenous, intraperitoneal, subcutaneous and/or intramuscular administration and in such form as to permit the biological activity of the active ingredient such as an endothelin receptor antagonist, contained therein to be effective, and which contains no additional components which are unacceptably toxic to a subject to which the formulation would be administered. These terms include both compositions that can be directly administered to a subject as well as compositions that need dilution or reconstitution into a conventional parenteral carrier solution. The liquid compositions for intravenous, intraperitoneal, subcutaneous or intramuscular administration may have the same ingredients in the same amounts, but compositions with different ingredients and/or different amounts also are contemplated.

"Liquid composition for oral administration" or "liquid formulation for oral administration" refers to a preparation which is suitable for oral administration and in such form as to permit the biological activity of the active ingredient such as an endothelin receptor antagonist, contained therein to be effective, and which contains no additional components which are unacceptably toxic to a subject to which the formulation would be administered. These terms include both compositions that can be directly administered to a subject as well as compositions that need dilution or reconstitution into a conventional oral carrier solution.

"Liver Fibrosis", also referred to as fibrosis, is characterized by the excess deposition of extracellular matrix components such as collagen in a regenerative or reactive process, resulting in tissue scarring in the liver. Extensive liver fibrosis may result in cirrhosis.

"Non-Alcoholic Steatohepatitis" or "NASH" refers to a form of inflammatory chronic liver disease where significant accumulation of fat in the liver occurs, and this accumulation is not associated with alcohol use.

"Portal hypertension", also referred to as "increased portal pressure" and variations thereof, refers to an increase in the blood pressure within the portal venous system above 5 mmHg. This increase is considered clinically significant when the pressure in the portal venous system is above 10 mmHg as determined by HVPG.

"Portopulmonary hypertension" refers to the coexistence of portal hypertension and pulmonary arterial hypertension and where no alternative cause of the pulmonary arterial hypertension has been established (e.g. collagen vascular disease, congenital heart disease, or certain drugs).

"Pulmonary arterial hypertension" also referred to as "PAH", refers to an increase in blood pressure in the pulmonary arterial system, specifically a mean pulmonary artery pressure above 25 mmHg at rest and a pulmonary capillary wedge pressure below 15 mmHg at rest.

"Progression of cirrhosis" and "progression of liver fibrosis" refer to the active process of fibrosis in the liver as seen in untreated chronic liver disease and is mainly characterized by the deposition of collagen in the liver, the loss of normal liver tissue architecture and the loss of hepatocytes, and usually diagnosed by biopsy. Clinically, it refers to the progressive increase in portal pressure and decrease in liver function over a period of time.

"Substantially continuous" means that the administration of the compounds and formulations according to the present invention may be constant or intermittent so long as the indicated blood levels of the ETA inhibitor are maintained, or the intended benefit is obtained.

"Treatment" (and variations thereof such as "treat" or "treating") as well as "prevention" (and variants thereof such as "prevent" or "preventing") refer to clinical intervention in an attempt to alter the natural course of the pathological condition of the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis.

Treatment of Portal Hypertension:

Various endothelin receptor antagonists are known, including selective ETA antagonists, such as, for example, sitaxentan, ambrisentan, atrasentan, BQ-123, zibotentan, bosentan, macitentan, tezosentan and darusentan. Preferred endothelin receptor antagonists are sitaxentan, ambrisentan, atrasentan, bosentan and macitentan. More preferred endothelin receptor antagonists are atrasentan, zibotentan and ambrisentan. Even more preferred endothelin receptor antagonists are atrasentan and ambrisentan. The most preferred antagonist is ambrisentan. None of these are approved for the treatment of portal hypertension, the major complications of cirrhosis or the progression of cirrhosis. Instead, some of these are approved for the treatment of pulmonary arterial hypertension (PAH).

Contrary to the methods and formulations of the present invention, the approved dosage and formulations of endothelin receptor antagonists for the treatment of PAH create plasma levels of the endothelin receptor antagonist that significantly antagonize the effects of endothelin on the ETB receptors as well as the effects of endothelin on the ETA receptors in subjects with portal hypertension thereby causing no effect or increased rather than decreased portal pressure. For example, ambrisentan, sold under the product name of Letairis® in the US and Volibris® in Europe, was approved for daily oral administration at a dosage strength of 5 mg and 10 mg. Plasma levels following one-time administration of Letairis® in patients without liver impairment often reach 700 ng/ml, and generally are found in the range of about 350 ng/ml or 670 ng/ml for the 5 mg and 10 mg doses, respectively. In patients with liver impairment, concentrations of ambrisentan are higher. Such concentrations are too high to be effective in treating portal hypertension and in fact are counterproductive because they contribute to the loss of intra-hepatic vasodilation and hence may increase the pressure in the portal venous system and induce fluid retention by the kidney.

In addition, subjects, who develop portal hypertension, in particular portal hypertension associated with cirrhosis, generally suffer from significant liver dysfunction and occasionally renal impairment. Because of these comorbidities, this patient population cannot metabolize administered medications effectively, resulting in a higher accumulation of the drug compared to subjects without liver and/or renal impairment. Thus, the blood level of ambrisentan, when administered daily for oral administration as approved for PAH, will achieve concentrations that are too high and steadily increase over a few days to a trough (i.e. pre-dose) concentration in blood that is well above the desired and effective concentration used in the present invention. These high concentrations may lead to the blockade of ETB receptor sites, which in turn leads to loss of intra-hepatic vasodilation and hence may aggravate the pressure in the portal venous system and induce fluid retention by the kidney.

Furthermore, the current approved formulations of ambrisentan for PAH are administered as a once a day drug at higher doses to achieve suitable trough (i.e. pre-dose) concentrations. However, the peak concentrations obtained following the administration of such drugs are too high and generally lead to the blockade of ETB receptor sites, which in turn leads to loss of intra-hepatic vasodilation and hence may aggravate the pressure in the portal venous system and induce fluid retention by the kidney.

Also, patients with liver disease often have decreased levels of total protein in their blood, particularly albumin, which generally results in elevated blood levels of the unbound fraction of the endothelin receptor antagonist, the unbound fraction being the active fraction of the drug in blood as it is not otherwise bound to circulating protein present in blood and free to bind to the endothelin receptor. Higher total concentrations of the unbound endothelin receptor therefore result in a higher blockade of the ETB receptor, which in turn leads to loss of intra-hepatic vasodilation and hence may aggravate the pressure in the portal venous system and induce fluid retention by the kidney.

Moreover, patients with portal hypertension have frequently difficulties to swallow solids, in particular when hepatic encephalopathy is present and in the elderly suffering from cirrhosis. As such, solid formulations of the drugs may be difficult to swallow and may lead to low compliance with the treatment regimen, unlike liquid formulations that are easier to swallow and provide for buccal absorption of the drug.

For all of these reasons, when administered at the approved dosage form and strength, Letairis® (ambrisentan) and other compounds approved to treat PAH are not effective to treat portal hypertension, the major complications of cirrhosis and the progression of cirrhosis. Moreover, use of approved PAH therapies to treat portal hypertension may be detrimental to portal pressure and may increase the incidence of renal adverse effects, exacerbate the incidence and severity of the complications of portal pressure, and/or conditions caused thereby.

Accordingly, the methods and formulations of the present invention contemplate the use of ETA antagonists to achieve much lower blood concentrations than are commonly used for approved therapies for PAH. In one embodiment of the present invention oral routes of administration, particularly solutions, drops, oral dispersible tablets, dispersible oral films, oral films and powders, are suitable for the various indications described in this application. In addition, preferred embodiments of the present invention also involve parenteral routes of administration, particularly intravenous, subcutaneous and transdermal.

In a preferred embodiment, the invention pertains to the use of ambrisentan or a liquid composition comprising ambrisentan in the treatment of portal hypertension, wherein ambrisentan is administered to a treated subject such that the plasma levels of ambrisentan are maintained below about 10 ng/ml. The invention hence pertains to ambrisentan for use in treating portal hypertension, wherein ambrisentan is administered to a treated subject such that the plasma levels of ambrisentan are maintained below about 10 ng/ml. Further, the invention provides a method for treating a subject suffering from portal hypertension wherein an effective amount of ambrisentan is administered to the subject, wherein ambrisentan is administered to a treated subject such that the plasma levels of ambrisentan are maintained below about 10 ng/ml. Lower concentrations of ambrisentan are required in patients with cirrhosis and portal hypertension as compared to ambrisentan concentrations needed in patients with acute kidney failure, as the unbound fraction of ambrisentan is higher because of low protein concentration in blood and the slower metabolism of ambrisentan by the liver. In patients with acute renal failure (such as the ones disclosed in WO 2017/158199), higher ambrisentan doses are needed to obtain an effective amount due to a faster metabolism and the presence of a higher amount of proteins in the blood capable of binding ambrisentan.

In a preferred embodiment, the invention pertains to the use of ambrisentan or a liquid composition comprising ambrisentan in the treatment of portal hypertension, wherein ambrisentan is administered to a treated subject such that the plasma levels of ambrisentan are maintained below about 10 ng/ml, and a reduction of portal pressure as determined by HVPG of at least 10%, preferably at least 20%, is obtained. The invention hence pertains to ambrisentan for use in treating portal hypertension, wherein ambrisentan is administered to a treated subject such that the plasma levels of ambrisentan are maintained below about 10 ng/ml, and a reduction of portal pressure as determined by HVPG of at least 10%, preferably at least 20%, is obtained. Further, the invention provides a method for treating a subject suffering from portal hypertension comprising administering ambrisentan wherein an effective amount of ambrisentan is administered to the subject, wherein ambrisentan is administered to a treated subject such that the plasma levels of ambrisentan are maintained below about 10 ng/ml, and a reduction of portal pressure as determined by HVPG of at least 10%, preferably at least 20%, is obtained. A reduction in HVPG of at least 10% considerably reduces the risk of complications from portal hypertension, such as variceal bleeding. Even more preferred is a reduction in HVPG of at least 20% as such a reduction generally leads to a reduction in mortality risk, risk of variceal bleeding, risk of rebleeding and ascites.

In a preferred embodiment, the invention pertains to the use of ambrisentan or a liquid composition comprising ambrisentan in the treatment of portal hypertension, wherein ambrisentan is administered to a treated subject such that the plasma levels of ambrisentan are maintained below about 10 ng/ml, and portal pressure as determined by HVPG is reduced to at most 12 mmHg, preferably at most 10 mmHg and most preferably at most 5 mmHg. The invention hence pertains to ambrisentan for use in treating portal hypertension, wherein ambrisentan is administered to a treated subject such that the plasma levels of ambrisentan are maintained below about 10 ng/ml, and portal pressure as determined by HVPG is reduced to at most 12 mmHg, preferably at most 10 mmHg and most preferably at most 5 mmHg. Further, the invention provides a method for treating a subject suffering from portal hypertension comprising administering ambrisentan wherein an effective amount of ambrisentan is administered to the subject, wherein ambrisentan is administered to a treated subject such that the plasma levels of ambrisentan are maintained below about 10 ng/ml, and portal pressure as determined by HVPG is reduced to at most 12 mmHg, preferably at most 10 mmHg and most preferably at most 5 mmHg.

In a preferred embodiment, the invention pertains to the use of ambrisentan or a liquid composition comprising ambrisentan in the treatment of portal hypertension associated with cirrhosis, wherein ambrisentan is administered to a treated subject such that the plasma levels of ambrisentan are maintained below about 10 ng/ml. The invention hence pertains to ambrisentan for use in treating portal hypertension associated with cirrhosis, wherein ambrisentan is administered to a treated subject such that the plasma levels of ambrisentan are maintained below about 10 ng/ml. Further, the invention provides a method for treating a subject suffering from portal hypertension associated with cirrhosis comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the treatment of portopulmonary hypertension, wherein ambrisentan is administered to a treated subject such that the plasma levels of ambrisentan are maintained below about 10 ng/ml. The invention hence pertains to ambrisentan for use in treating portopulmonary hypertension, wherein ambrisentan is administered to a treated subject such that the plasma levels of ambrisentan are maintained below about 10 ng/ml. Further, the invention provides a method for treating a subject suffering from portopulmonary hypertension comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the treatment of ascites, wherein ambrisentan is administered to a treated subject such that the plasma levels of ambrisentan are maintained below about 10 ng/ml. The invention hence pertains to ambrisentan for use in treating ascites, wherein ambrisentan is administered to a treated subject such that the plasma levels of ambrisentan are maintained below about 10 ng/ml. Further, the invention provides a method for treating a subject suffering from ascites comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the prophylactic treatment of variceal bleeding, wherein ambrisentan is administered to a treated subject such that the plasma levels of ambrisentan are maintained below about 10 ng/ml. The invention hence pertains to ambrisentan for use in prophylactically treating variceal bleeding, wherein ambrisentan is administered to a treated subject such that the plasma levels of ambrisentan are maintained below about 10 ng/ml. Further, the invention provides a method for prophylactically treating a subject at risk of variceal bleeding comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the treatment of variceal bleeding, wherein ambrisentan is administered to a treated subject such that the plasma levels of ambrisentan are maintained below about 10 ng/ml. The invention hence pertains to ambrisentan for use in treating variceal bleeding, wherein ambrisentan is administered to a treated subject such that the plasma levels of ambrisentan are maintained below about 10 ng/ml. Further, the invention provides a method for treating a subject suffering from variceal bleeding comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the treatment of jaundice, wherein ambrisentan is administered to a treated subject such that the plasma levels of ambrisentan are maintained below about 10 ng/ml. The invention hence pertains to ambrisentan for use in treating jaundice, wherein ambrisentan is administered to a treated subject such that the plasma levels of ambrisentan are maintained below about 10 ng/ml. Further, the invention provides a method for treating a subject suffering from jaundice comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the treatment of hepatic encephalopathy, wherein ambrisentan is administered to a treated subject such that the plasma levels of ambrisentan are maintained below about 10 ng/ml. The invention hence pertains to ambrisentan for use in treating hepatic encephalopathy, wherein ambrisentan is administered to a treated subject such that the plasma levels of ambrisentan are maintained below about 10 ng/ml. Further, the invention provides a method for treating a subject suffering from hepatic encephalopathy comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the prophylactic treatment of the progression of cirrhosis, wherein ambrisentan is administered to a treated subject such that the plasma levels of ambrisentan are maintained below about 10 ng/ml. The invention hence pertains to ambrisentan for use in the prophylactic treatment of progression of cirrhosis, wherein ambrisentan is administered to a treated subject such that the plasma levels of ambrisentan are maintained below about 10 ng/ml. Further, the invention provides a method for prophylactically treating a subject who may be at risk of cirrhosis progression comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the prophylactic treatment of the progression of liver fibrosis, wherein ambrisentan is administered to a treated subject such that the plasma levels of ambrisentan are maintained below about 10 ng/ml. The invention hence pertains to ambrisentan for use in the prophylactic treatment of progression of liver fibrosis, wherein ambrisentan is administered to a treated subject such that the plasma levels of ambrisentan are maintained below about 10 ng/ml. Further, the invention provides a method for prophylactically treating a subject who may be at risk of liver fibrosis progression comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the treatment of Non-Alcoholic Steatohepatitis (NASH), wherein ambrisentan is administered to a treated subject such that the plasma levels of ambrisentan are maintained below about 10 ng/ml. The invention hence pertains to ambrisentan for use in the treatment of Non-Alcoholic Steatohepatitis (NASH), wherein ambrisentan is administered to a treated subject such that the plasma levels of ambrisentan are maintained below about 10 ng/ml. Further, the invention provides a method for treating a subject who suffers from Non-Alcoholic Steatohepatitis (NASH) comprising administering ambrisentan wherein an effective amount of ambrisentan is administered to the subject, wherein ambrisentan is administered to a treated subject such that the plasma levels of ambrisentan are maintained below about 10 ng/ml.

In a preferred embodiment, the invention pertains to the use of ambrisentan or a liquid composition comprising ambrisentan in the treatment of subjects suffering from Non-Alcoholic Steatohepatitis (NASH) and reducing the progression of liver fibrosis and/or reduction of portal hypertension, wherein ambrisentan is administered to a treated subject such that the plasma levels of ambrisentan are maintained below about 10 ng/ml. The invention hence pertains to ambrisentan for use in the treatment of subjects suffering from Non-Alcoholic Steatohepatitis (NASH) and reducing the progression of liver fibrosis and/or reduction of portal hypertension, wherein ambrisentan is administered to a treated subject such that the plasma levels of ambrisentan are maintained below about 10 ng/ml. Further, the invention provides a method for treating a subject who suffers from Non-Alcoholic Steatohepatitis (NASH) and reducing the progression of liver fibrosis and/or reduction of portal hypertension comprising administering ambrisentan wherein an effective amount of ambrisentan is administered to the subject, wherein ambrisentan is administered to a treated subject such that the plasma levels of ambrisentan are maintained below about 10 ng/ml.

The above embodiments also apply to zibotentan and atrasentan, and their individual embodiments are also included.

Therapeutic Levels of ETA Antagonist:

In a preferred embodiment of the present invention, the ETA antagonist is ambrisentan. For purposes of the present invention, ambrisentan is administered to a treated subject such that the plasma levels of that compound preferably are maintained below about 10 ng/ml, preferably below about 8 ng/ml, more preferably below about 6 ng/ml, and most preferably below about 5 ng/ml, and generally, the plasma level of ambrisentan is at least 0.001 ng/ml, preferably at least 0.01 ng/and most preferably at least 0.1 ng/ml. The said plasma levels of ambrisentan refer to the overall ambrisentan concentration in the blood plasma, which include both the ambrisentan bound to proteins present in the blood and the free, unbound ambrisentan present in the blood. The plasma levels or concentration of both bound and unbound ambrisentan can be determined using conventional techniques.

In a further embodiment, ambrisentan is administered to a treated subject such that the plasma levels of unbound ambrisentan (i.e. not bound to protein) are at most 0.1 ng/ml, preferably at most 0.08 ng/ml, more preferably at most 0.06 ng/ml, and most preferably at most 0.05 ng/ml, and generally at least 0.00001 ng/ml, preferably at least 0.0001 ng/ml, and most preferably at least 0.001 ng/ml. The plasma levels or concentration of the free ambrisentan in the blood plasma can be determined by separating the ambrisentan bound to protein and determining the ambrisentan concentration using conventional analytical techniques.

Administration Protocols:

It is contemplated that ETA antagonists according to the present invention will be administered for a period of time in which such administration improves portal pressure and provides clinical benefit. In the case the ETA antagonist, in particular ambrisentan, is used to treat portal hypertension and its complications which is of a temporary nature, the ETA antagonist will be administered for a period of time of up to about twenty-eight days, preferably up to about fourteen days, and most preferably for about seven days. The administration of the ETA antagonist, when administered intravenously, will be substantially continuous.

However, a physician may choose to administer the ETA antagonist in a repeated cycle of, for example, four days, with one or more intervening days in which the ETA antagonist is not administered.

In the case the ETA antagonist, in particular ambrisentan, is used to treat portal hypertension and its complications which may be persistent, e.g. progression of cirrhosis, portal hypertension associated with cirrhosis, or other complications of cirrhosis (e.g. portopulmonary hypertension, ascites, variceal bleeding, jaundice or hepatic encephalopathy), the ETA antagonist will be administered for a prolonged period of time on a daily basis or less often. The prolonged period can be the period up to, during and/or after a solid organ transplant, e.g. of a kidney or of a liver, or the treatment can be prolonged until the patient dies.

In one embodiment of the invention, the frequency of administration of the ETA antagonist, preferably ambrisentan, is more than once a day, more preferably twice a day, and most preferably three times a day. In this way, the concentration of the antagonist in the blood plasma does not exceed 10 ng/mL at any given time, and the actual plasma concentration of the ETA antagonist, preferably ambrisentan, remains sufficiently high to maintain the lower portal pressure.

Formulations:

Formulations suitable for use in the aforementioned treatments and indications are formulations that upon administration enable the maintenance of the blood plasma level of the ETA antagonist, preferably ambrisentan, below 10 ng/ml. The inventors have found that formulations that are administered orally are suitable, in particular formulations allowing the ETA antagonist, preferably ambrisentan, to be released in the patient's mouth. Examples of such formulations include oral solutions (OS), orally disintegrating films (ODF), orally disintegrating tablets (ODT) and powders. Doses that are not administered in solid form have the additional advantage of being appropriate for subjects who have difficulty in swallowing solids, such as subjects suffering from a neurological deficit, neuropsychiatric impairment or hepatic encephalopathy. Oral administration in the form of solution has the advantage that the antagonist is also absorbed in a shorter period of time than alternative administration methods because of absorption in the mouth mucosa, and the desired blood concentration can be reached more readily and more effectively than with solid oral formulations. Additionally, doses administered in the form of oral solutions such as drops can be adjusted in a simple manner, which may be necessary in view of the metabolic and functional characteristics of the subject.

In one embodiment, the formulation is a parenteral formulation. The invention further pertains to a patch comprising the ETA antagonist, preferably ambrisentan.

The invention further pertains to an oral solution. The oral solution of the invention comprises a solvent and an ETA, preferably ambrisentan.

The solvent can be any solvent known in the art that can be suitably used in oral solutions of the invention. Examples of solvents include water, alcohols such as ethanol, glycerin, polyethylene glycol such as PEG300, PEG400 and PEG600; propylene glycol, N-methyl-2-pyrrolidone, and combinations of two or more of these solvents. Of these solvents water, ethanol, propylene glycol and polyethylene glycol or combinations comprising predominantly any one of these solvents are preferred. In another preferred embodiment, the composition of the invention does not contain water as solvent, and more preferably the composition is free from water.

In one embodiment of the invention, the oral solution comprises the solvent in an amount of at most 99.999% by weight (wt %), based on the total weight of the oral solution. Preferably, the solvent is present in an amount of at most 99.995 wt %, more preferably at most 99.99 wt %, and most preferably at most 99.985 wt %, and preferably at least 99 wt %, more preferably at least 99.5 wt %, even more preferably at least 99.8 wt %, even more preferably at least 99.9 wt % and most preferably at least 99.95 wt %, based on the total weight of the oral solution.

In one embodiment of the invention, the oral solution comprises ambrisentan in an amount of at most 1% by weight (wt %), based on the total weight of the oral solution. Preferably, ambrisentan is present in an amount of at most 0.5 wt %, more preferably at most 0.2 wt %, even more preferably at most 0.1 wt % and most preferably at most 0.05 wt %, and preferably at least 0.0001 wt %, more preferably at least 0.0005 wt %, even more preferably at least 0.001 wt % and most preferably at least 0.0015 wt %, based on the total weight of the oral solution.

The oral solution of the invention may further comprise OS excipients. The OS excipients may be any excipient known in the art that can be suitably used in oral solutions of the invention. Examples of such OS excipients include surfactants such as sodium dodecyl sulfate, sodium lauryl sulfate, polyoxyethylene sorbitan fatty acids (sold under tradename Tween®), sorbitan fatty acid esters (sold under tradename Span®) and polyoxyethylene stearates; rheology modifiers such as cellulose derivatives, alginic acid and polyvinyl pyrrolidone; preservatives such as boric acid, borate salts, sorbic acid, sorbate salts and phenolics; antioxidants such as sodium formaldehyde sulphoxylate, butylated hydroxyanisol and butylated hydroxytoluene (BHT); flavors such as mint, licorice and sucralose; sweetening agents such as fructose, mannitol, sorbitol, aspartame and saccharose; saliva stimulating agents such as citric acid, malic acid, tartaric acid, ascorbic acid and lactic acid; and coloring agents such as titanium dioxide, amaranth, sunset yellow and red iron oxide.

In one embodiment of the invention, the oral solution comprises the OS excipient in an amount of at most 15% by weight (wt %), based on the total weight of the oral solution. Preferably, the OS excipient is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the oral solution.

Typically, the total amount of the endothelin receptor antagonist, the solvent and the OS excipients (when present) add up to 100 wt % in the oral solution of the invention.

The invention further pertains to orally disintegrating films, also referred to as "ODF" or "orodispersible films". The orally disintegrating film of the invention comprises a water-soluble polymer and an ETA, preferably ambrisentan.

The water-soluble polymer can be any polymer known in the art that can be suitably used in ODFs of the invention. Examples of such polymers include natural polymers such as starch, polymerized rosin, pullulan, sodium alginate, pectin, carrageenan, chitosan, gelatin and maltodextrins; and synthetic polymers such as polyvinyl alcohol (PVA), polyethylene oxide (PEO), hydroxypropyl methyl cellulose (HPMC), sodium carboxymethyl cellulose (CMC), polyvinyl pyrrolidone (PVP) and hydroxypropyl cellulose (HPC).

In one embodiment of the invention, the ODF comprises the water-soluble polymer in an amount of at most 99.999% by weight (wt %), based on the total weight of the ODF. Preferably, the polymer is present in an amount of at most 99.995 wt %, more preferably at most 99.99 wt %, and most preferably at most 99.985 wt %, and preferably at least 99 wt %, more preferably at least 99.5 wt %, even more preferably at least 99.8 wt %, even more preferably at least 99.9 wt % and most preferably at least 99.95 wt %, based on the total weight of the ODF.

In one embodiment of the invention, the ODF comprises ambrisentan in an amount of at most 1% by weight (wt %), based on the total weight of the ODF. Preferably, ambrisentan is present in an amount of at most 0.5 wt %, more preferably at most 0.2 wt %, even more preferably at most 0.1 wt % and most preferably at most 0.05 wt %, and preferably at least 0.0001 wt %, more preferably at least 0.0005 wt %, even more preferably at least 0.001 wt % and most preferably at least 0.0015 wt %, based on the total weight of the ODF.

The ODF of the invention may further comprise a plasticizer. The plasticizer can be any plasticizer known in the art that can be suitably used in ODFs of the invention. Examples of such plasticizers include polyethylene glycol, glycerol, diethyl phthalate, triethyl citrate and tributyl citrate.

In one embodiment of the invention, the ODF comprises the plasticizer in an amount of at most 15% by weight (wt %), based on the total weight of the ODF. Preferably, the plasticizer is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the ODF.

The ODF of the invention may further comprise a surfactant. The surfactant can be any surfactant known in the art that can be suitably used in ODFs of the invention. Examples of such surfactants include benzalkonium chloride, sorbitan-based surfactants such as Tween® 20 and Tween 80, block-copolymer of polyethylene glycol and polypropylene glycol such as Poloxamer® 407 and sodium lauryl sulfate.

In one embodiment of the invention, the ODF comprises the surfactant in an amount of at most 15% by weight (wt %), based on the total weight of the ODF. Preferably, the surfactant is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the ODF.

The ODF of the invention may further comprise ODF excipients. The ODF excipients may be any excipient known in the art that can be suitably used in ODFs of the invention. Examples of such ODF excipients include flavors such as mint, licorice and sucralose; sweetening agents such as fructose, mannitol, sorbitan, aspartame and saccharose; saliva stimulating agents such as citric acid, malic acid, tartaric acid, ascorbic acid and lactic acid; and coloring agents such as titanium dioxide.

In one embodiment of the invention, the ODF comprises the ODF excipient in an amount of at most 15% by weight (wt %), based on the total weight of the ODF. Preferably, the ODF excipient is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the ODF.

Typically, the total amount of the endothelin receptor antagonist, the water-soluble polymer and additional excipients including the plasticizer, surfactant and ODF excipients (when present) add up to 100 wt % in the ODF of the invention.

The invention further pertains to orally disintegrating tablets, also referred to as "ODT" or "orodispersible tablets". The orally disintegrating tablet of the invention comprises a disintegrant, an ETA, preferably ambrisentan, and optionally a binder.

The disintegrant, also referred to as "superdisintegrant" can be any disintegrant known in the art that can be suitably used in ODTs of the invention. Examples of such disintegrants include crosslinked polyvinyl pyrrolidone such as crospovidone; microcrystalline cellulose; crosslinked cellulose such as Crosscarmellose®, Ac-Di-Sol®, Primellose® and Vivasol®; crosslinked starch such as sodium starch glycolate; sodium carboxymethyl cellulose and hydroxypropyl ethyl cellulose; pregelatinized starch; soya polysaccharides; calcium silicate, and crosslinked alginic acid such as alginic acid NF.

In one embodiment of the invention, the ODT comprises the disintegrant in an amount of at most 99.9% by weight (wt %), based on the total weight of the ODT. Preferably, the disintegrant is present in an amount of at most 99.5 wt %, more preferably at most 99 wt %, and most preferably at most 98 wt %, and preferably at least 85 wt %, more preferably at least 90 wt %, even more preferably at least 92 wt %, even more preferably at least 93 wt % and most preferably at least 95 wt %, based on the total weight of the ODT.

The binder can be any binder known in the art that can be suitably used in ODTs of the invention. Examples of such binders include polyvinyl pyrrolidone (PVP), polyvinyl alcohol (PVA) and hydroxypropyl methyl cellulose (HPMC).

In one embodiment of the invention, the ODT comprises the binder in an amount of at most 15% by weight (wt %), based on the total weight of the ODT. Preferably, the binder is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the ODT.

In one embodiment of the invention, the ODT comprises ambrisentan in an amount of at most 1% by weight (wt %), based on the total weight of the ODT. Preferably, ambrisentan is present in an amount of at most 0.5 wt %, more preferably at most 0.2 wt %, even more preferably at most 0.1 wt % and most preferably at most 0.05 wt %, and preferably at least 0.0001 wt %, more preferably at least 0.0005 wt %, even more preferably at least 0.001 wt % and most preferably at least 0.0015 wt %, based on the total weight of the ODT.

The ODT of the invention may further comprise ODT excipients. The ODT excipients may be any excipient known in the art that can be suitably used in ODTs of the invention. Examples of such ODT excipients include lubricants such as stearic acid, magnesium stearate, zinc stearate, calcium stearate, talc, polyethylene glycol, liquid paraffin, magnesium lauryl sulfate and colloidal silicon dioxide; fillers such as mannitol, sorbitol, xylitol, calcium carbonate, magnesium carbonate, calcium phosphate, calcium sulfate, pregelatinized starch, magnesium trisilicate and aluminium hydroxide; surfactants such as sodium dodecyl sulfate, sodium lauryl sulfate, polyoxyethylene sorbitan fatty acids (sold under tradename Tween®), sorbitan fatty acid esters (sold under tradename Span®) and polyoxyethylene stearates; flavors such as mint, licorice and sucralose; sweetening agents such as fructose, mannitol, sorbitol, aspartame and saccharose; saliva stimulating agents such as citric acid, malic acid, tartaric acid, ascorbic acid and lactic acid; and coloring agents such as titanium dioxide, amaranth, sunset yellow and red iron oxide.

In one embodiment of the invention, the ODT comprises the ODT excipient in an amount of at most 15% by weight (wt %), based on the total weight of the ODF. Preferably, the ODT excipient is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the ODT.

Typically, the total amount of the endothelin receptor antagonist, the disintegrant, the binder and the ODT excipients (when present) add up to 100 wt % in the ODT of the invention.

In one embodiment, the formulation of the ETA antagonist, preferably ambrisentan, according to the invention is a parenteral formulation. Other forms of parenteral administration also are contemplated, such as subcutaneous, transdermal, intraperitoneal and intramuscular. Of these forms, subcutaneous is preferred. Doses that are not administered orally have the additional advantage of being appropriate for subjects who are unable to swallow, such as subjects suffering from a neurological deficit or hepatic encephalopathy or those subjects under anesthesia or similar conditions. Parenteral administration has the advantage that the antagonist is more effective in a shorter period of time than alternative administration methods, and the desired blood concentration can be reached readily. Additionally, the dose can be adjusted in a simple manner, which may be necessary in view of the metabolic and functional characteristics of the subject.

The present invention further pertains to a liquid composition for parenteral administration comprising an endothelin receptor antagonist, a buffer and a solvent. Preferably, the invention pertains to a liquid composition for parenteral administration comprising ambrisentan, a buffer and a solvent.

The liquid composition of the invention is preferably substantially free of particles. More preferably, the liquid composition of the invention is free of particles. With "particles" is meant any kind of solids including particles of the endothelin receptor antagonist, dust particles or polymeric particles. The term "substantially free of particles" refers to solid particles being present in amounts and sizes as prescribed in the Pharmacopeia and acceptable according to regulatory standards.

In one embodiment of the invention, the liquid compositions comprise the endothelin receptor antagonist, preferably ambrisentan, in an amount of at most 15% by weight (wt %), based on the total weight of the liquid composition. Preferably, the endothelin receptor antagonist, preferably ambrisentan, is present in an amount of at most 10 wt %, more preferably at most 5 wt %, even more preferably at most 2 wt % and most preferably at most 1 wt %, and preferably at least 0.00001 wt %, more preferably at least 0.0001 wt %, even more preferably at least 0.0005 wt % and most preferably at least 0.001 wt %, based on the total weight of the liquid composition.

In one embodiment of the invention, the liquid composition comprises the buffer in an amount of at most 15% by weight (wt %), based on the total weight of the liquid composition. Preferably, the buffer is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the liquid composition.

Suitable solvents for use in the compositions of the invention include water, alcohols such as ethanol, glycerin, polyethylene glycol such as PEG300, PEG400 and PEG600; propylene glycol, N-methyl-2-pyrrolidone, and combinations of two or more of these solvents. Of these solvents water, ethanol, propylene glycol and polyethylene glycol or combinations comprising predominantly any one of these solvents are preferred. In another preferred embodiment, the composition of the invention does not contain water as solvent, and more preferably the composition is free from water.

In one embodiment of the invention, the liquid composition comprises the solvent in an amount of at least 85% by weight (wt %), based on the total weight of the liquid composition. Preferably, the solvent is present in an amount of at least 90 wt % and most preferably at least 92 wt %, and preferably at most 99.9 wt %, more preferably at most 98 wt %, and most preferably at most 95 wt %, based on the total weight of the liquid composition. Typically, the total amount of the endothelin receptor antagonist, the buffer, the solvent and additional excipients (when present) add up to 100 wt % in the liquid compositions of the invention.

When a buffer is present in the liquid composition, the buffer used in the composition of the invention may be any buffer known in the art which can be suitably used for parenteral administration. The buffer generally serves to maintain the composition at a constant pH, in particular upon storage and when the composition is moderately diluted. In one embodiment of the invention, the buffer is chosen such that the pH of the composition is generally between 6 and 12, preferably the pH is at least 6.5, more preferably at least 7, and preferably the pH is at most 10, and more preferably at most 9. Particularly preferred are compositions comprising ambrisentan having a pH of at least 9, as these compositions typically have a better stability and may have a higher concentration of ambrisentan.

In an embodiment of the invention, the pH of the resulting parenteral composition after adding the concentrated liquid composition of the invention is generally between 6 and 12, preferably the pH is at least 6.5, more preferably at least 7, and preferably the pH is at most 9, and more preferably at most 8.

Examples of suitable buffers include ammonium acetate, arginine, sodium benzoate, disodium citrate, trisodium citrate, diethanol amine, hydrobromic acid, monoethanol amine, phosphoric acid, monobasic sodium phosphate, dibasic sodium phosphate, tribasic sodium phosphate, monobasic potassium phosphate, dibasic potassium phosphate, tris (hydroxymethyl)methylamine (Tromethamine or Tris), 4-2-hydroxyethyl-1-piperazineethanesulfonic acid (HEPES), and 2(R)-2-(methylamino)succinic acid, and combinations of two or more of said buffers. It is also contemplated to combine one or more of the mentioned buffers with one or more buffer agents having a pKa below 6 and above 10 as long as the overall pH of the composition of the invention is between 6 and 10.

The liquid composition may be comprised of other components commonly used in liquid compositions for parenteral administration. When the liquid formulation of the invention comprises components other than the endothelin receptor antagonist or ambrisentan, the buffer and the solvent, the total amount of the endothelin receptor antagonist or ambrisentan, the buffer, the solvent, and the other components, such as excipients, add up to 100 wt % of the total weight of the liquid composition.

The compositions of the invention may further comprise excipients. Suitable excipients are known in the art. Such excipients include, stabilizers and/or bulking agents such as mannitol, sucrose, trehalose, polyethylene glycol; tonicity agents like dextrose, sodium chloride, glycerol, glycerin and mannitol; viscosity enhancers or reducers such as sodium carboxymethyl cellulose, acacia, gelatin, methyl cellulose and polyvinyl pyrrolidone; surfactants like polyoxyethylene sorbitan monooleate (Tween 80), sorbitan monooleate, polyoxyethylene sorbitan monolaurate (Tween 20), polyoxyethylene polyoxypropylene copolymers (Pluronics), and lecithin; chelates like calcium disodium ethylenediaminetetra acetic acid (EDTA), disodium EDTA, sodium EDTA, calcium versetamide Na, calteridol and diethylenetriamine-penta acetic acid (DTPA); antioxidants such as acetyl cysteine, sulfurous acid salts (bisulfites and metasulfites), antimicrobial agents like phenol, meta-cresol, benzyl alcohol, methyl paraben, propyl paraben and butyl paraben; and other adjuvants. It is appreciated that some excipients may have multiple properties.

In one embodiment of the invention, the liquid composition comprises the excipient in an amount of at most 15% by weight (wt %), based on the total weight of the liquid composition. Preferably, the buffer is present in an amount of at most 10 wt %, more preferably at most 8 wt %, even more preferably at most 7 wt % and most preferably at most 5 wt %, and preferably at least 0.01 wt %, more preferably at least 0.1 wt %, even more preferably at least 0.5 wt % and most preferably at least 1 wt %, based on the total weight of the liquid composition.

In a preferred embodiment, the liquid composition of the invention is isotonic. In a preferred embodiment, the liquid composition of the invention is sterile.

The liquid compositions of the invention can be prepared using conventional techniques.

Liquid compositions for parenteral administration can be provided in any suitable container including but not limited to an ampoule, a vial, a pre-filled syringe, a cartridge for a subcutaneous pump, a cartridge for a subcutaneous pen, medication reservoir for a subcutaneous pump or an IV container such as an IV bag or bottle. The concentration of the ETA receptor antagonist may differ depending on the container used in order to achieve improved portal pressure and clinical benefit.

The liquid compositions may be administered directly to the subject. They also initially may be stored or formulated in concentrated forms that will be diluted in an appropriate parenteral solution, such as conventional physiological solutions for intravenous administration, pharmaceutically acceptable organic solvents such as propylene glycol and ethanol, or combinations thereof, before being administered. Appropriate buffers, excipients and preservatives are conventional. Examples of such parenteral solutions include saline solutions (sterile aqueous solutions of sodium chloride), Ringer's lactate solution, Hartmann's solution (comprising sodium lactate), dextrose-containing solutions (like D5W or D10W) and solutions combining any of the foregoing ingredients (like D5NS or D5LR), and pharmaceutically acceptable organic solvents such as propylene glycol and ethanol, or combinations thereof.

The liquid compositions may be added to the conventional parenteral solutions using conventional techniques. The dilution factor of the endothelin receptor antagonist may be at least 5, which means that, for example, 50 ml of the liquid composition of the invention is added to 200 ml of the conventional parenteral solutions. Preferably, the dilution factor is at least 10 and most preferably at least 15, and generally at most 100, preferably at most 75, and most preferably at most 50.

The invention further pertains to transdermal patches. The transdermal patch may be any known transdermal patch in the art comprising the ETA antagonist, preferably ambrisentan. The transdermal patch of the invention generally comprises the ETA antagonist, preferably ambrisentan, a polymer matrix and/or drug reservoir, optionally a permeation enhancer, optionally a pressure sensitive adhesive, a backing laminate, a release liner and optionally other transdermal patch excipients. Such transdermal patches may be a single-layer-drug-in-adhesive system, a reservoir system, a matrix system such as a drug-in-adhesive system or a matrix-dispersion system, and a micro-reservoir system such as described in Sharma (in Organic & Medicinal Chem IJ 7(2), OMCIJ. MS. ID. 555707 (2018), pp. 1-5).

The polymer matrix or drug reservoir can be any polymer known in the art that can be suitably used in transdermal patches of the invention. Examples of such polymer matrices include natural polymers such as cellulose derivatives, zein, gelatin, shellac, waxes, gums, natural rubber; synthetic elastomers such as polybutadiene, hydrin rubber, silicon rubber, polyisobutylene, acrylonitrile, neoprene and butyl rubber; and synthetic polymers such as polyvinyl alcohol, polyvinyl chloride, polyethylene, polypropylene, polyacrylate, polyamide, polyuria, polyvinyl pyrrolidone and polymethylmethacrylate.

The permeation enhancer can be any permeation enhancer known in the art that can be suitably used in transdermal patches of the invention. Examples of such permeation enhancers include dimethyl sulphoxide (DMSO), azone, pyrrolidones such as methyl pyrrolidone; fatty acids such as lauric acid, myristyc acid, oleic acid, linoleic acid and capric acid; essential oils such as terpenes and terpenoids; oxazolidinones such as 4-decyloxazolidin-2-one; and urea.

The pressure sensitive adhesive can be any pressure sensitive adhesive known in the art that can be suitably used in transdermal patches of the invention. Examples of such pressure sensitive adhesive include polyacrylates, polyisobutylene and silicon-based adhesives.

The backing laminate can be any backing laminate known in the art that can be suitably used in transdermal patches of the invention. Examples of such backing laminates include vinyl, polyethylene and polyester films.

The release liner can be any release liner known in the art that can be suitably used in transdermal patches of the invention. Examples of such release liners include non-occlusive release liners made of paper fabric, for instance; and occlusive release liners made of, for example, polyethylene and polyvinylchloride.

The transdermal patch of the invention may further comprise TP excipients. The TP excipients may be any excipient known in the art that can be suitably used in transdermal patches of the invention. Examples of such TP excipients include solvents such methanol, chloroform, methanol, acetone, isopropanol and dichloromethane; and plasticizers such as dibutyl phthalate, triethyl citrate, polyethylene glycol and polypropylene glycol.

The size, thickness and amounts of the various features used in the transdermal patch of the invention are conventionally used values.

In general, it is contemplated that persons skilled in the art will adjust the amount of ETA (or ambrisentan) and formulation by conventional means as is appropriate for administration to a particular subject.

The above embodiments of the liquid composition of the invention also apply to zibotentan and atrasentan, and their individual embodiments are also included.

The above embodiments of the orodispersible tablet composition of the invention also apply to zibotentan and atrasentan, and their individual embodiments are also included.

The above embodiments of the orodispersible film composition of the invention also apply to zibotentan and atrasentan, and their individual embodiments are also included.

The above embodiments of the transdermal patch composition of the invention also apply to zibotentan and atrasentan, and their individual embodiments are also included.

EXAMPLES

Examples 1 and 2: Preparation of Ambrisentan Oral Solutions

Two oral solutions comprising respectively 500 µg (Example 1) and 1 mg (Example 2) ambrisentan per ml of solvent were prepared. First 5 mL Ethanol and 90 mL propylene glycol 1,2 were mixed together. The resulting solution was heated to 40° C. Subsequently, the necessary amount of ambrisentan was added and the solution was stirred until the ambrisentan completely dissolved. The resulting solution was cooled and sterilized by passing the solution through a suitable filter. The resulting liquid composition is in accordance with the invention and contains 500 µg/mL of ambrisentan (Example 1) and 1 mg/mL of ambrisentan (Example 2). Analyzing the resulting liquid composition showed that ambrisentan remained stable and no decomposition was observed.

Example 3: Preparation of Ambrisentan Parenteral Formulation

A liquid composition comprising 5 mg ambrisentan per ml of solvent was prepared. First 2750 g Ethanol and 2750 g propylene glycol 1,2 were mixed together. The resulting solution was heated to 40° C. Subsequently, 30.27 g of ambrisentan were added to 5469.7 g of the solution. The solution was stirred until the ambrisentan completely dissolved. The resulting solution was cooled and sterilized by passing the solution through a suitable filter. The resulting liquid composition is in accordance with the invention and contains 5 mg/mL of ambrisentan. Analyzing the resulting liquid composition showed that ambrisentan remained stable and no decomposition was observed.

The solution obtained can be diluted in various ratios with an aqueous saline and other buffers having pH 6 and above. It is anticipated that prior to human administration, the physician will mix with sterile aqueous solution to obtain the desired ambrisentan concentration.

Stability Tests

The liquid composition of Example 3 was tested for its stability. The tests were conducted by applying 5 ml of the solution in vials which are stored at different temperatures, i.e. 5° C. and 25° C. for up to 180 days in conditioned chambers. The solutions did not reveal any chemical and physical decomposition of ambrisentan at 5° C. and some degradation was observed at 25° C.

Examples 4-9: Water-Free Ambrisentan Parenteral Formulations

Various compositions in accordance with the invention and Example 3 above using a variety of solvents were prepared. To ambrisentan, the solvents or solvent mixtures were added and stirred. An overview of the ingredients of these compositions are presented in the Table 1 below.

TABLE 1

Water-free ambrisentan formulations

| Example | Solvent | Ambrisentan concentration (mg/ml) |
|---|---|---|
| 4 | Ethanol/propylene glycol 1,2 (3:7) | 1 |
| 5 | Ethanol/propylene glycol 1,2 (3:7) | 10 |
| 6 | Ethanol/polyethyleneglycol 300 (3:7) | 10 |
| 7 | Ethanol | 1 bis 40 |
| 8 | Propylene glycol 1,2 | 1 bis 10 |
| 9 | Polyethyleneglycol 300 | 1 bis 20 |

In addition to the above examples further binary and tertiary solutions can be prepared for this purpose.

The invention described in this specification generally relates to methods and formulations for the treatment and prevention of portal hypertension comprising the administration of ETA antagonists. While certain exemplary embodiments have been described above in detail and, it is to be understood that such embodiments and examples are merely illustrative of and not restrictive of the broad invention. In particular, it should be recognized that the teachings of the invention apply to variations of the preferred embodiments that are specifically discussed. Modifications, substitutions, changes and equivalents will now occur to those skilled in the art. Thus, it will be understood that the invention is not limited to the particular embodiments or arrangements disclosed, but is rather intended to cover any changes, adaptations or modifications which are within the scope and spirit of the invention as defined by the appended claims.

Example 10

A series of experiments were performed to determine whether low concentrations of ambrisentan in blood are effective in reducing hepatic portal pressure in patients with pre-existing portal hypertension and whether these concentrations are more effective when compared to higher concentrations of ambrisentan. In the context of a clinical study (ClinicalTrials.gov Identifier: NCT03827200), ambrisentan was administered to 8 adult subjects with a history of cirrhosis and portal hypertension. Subjects were included in the study if they had a history of moderate to severe ascites, a common complication of portal hypertension. A liquid formulation of ambrisentan was used, consisting of a solution of propylene glycol:ethanol (50:50 w/w) and ambrisentan at a concentration of 5 mg/mL. The solution was reconstituted prior to administration in water or propylene glycol. All subjects were treated for 14 days. Portal pressure was estimated in this study by means of the Hepatic Vein Pressure Gradient (HVPG), the current gold standard to evaluate the degree of portal hypertension in adults with cirrhosis (as described in Bosch, J., Abraldes, J. G., Berzigotti, A., & Garcia-Pagan, J. C. (2009). *The clinical use of HVPG measurements in chronic liver disease. Nature Reviews Gastroenterology & Hepatology*, 6(10), 573-582). HVPG was measured at baseline and prior to the first administration of ambrisentan. Post-baseline values for HVPG were obtained at 90 minutes following the administration of the first dose of ambrisentan. After 14 days of treatment, HVPG was determined at trough (prior to the last dose) and 90 minutes following the last dose of ambrisentan. Two dose groups were evaluated in this study. In the high dose group, 4 subjects were administered 50 µg ambrisentan on day 1 subcutaneously, followed by 100 µg of ambrisentan twice a day orally for 13 days, for a total daily dose of 200 µg. On day 14, subjects in the high dose group received a final dose of 50 µg ambrisentan subcutaneously. In the low dose group, 4 subjects were administered 10 µg ambrisentan on day 1 subcutaneously, followed by 14 µg of ambrisentan once a day orally for 13 days. On day 14, subjects in the low dose group received a final dose of 10 µg ambrisentan subcutaneously.

A pharmacokinetic analysis of the high dose group indicated that the twice daily administration of 100 µg of ambrisentan for 13 days resulted in steady-state trough ambrisentan plasma concentrations of about 10 ng/mL. The administration of 50 µg of ambrisentan at day 14 resulted in concentrations of 18 ng/mL at 2 hours post-administration. With the assumption that ambrisentan displays linear pharmacokinetics in this concentration range, concentrations in the low dose group were estimated to be between 5 and 14-fold lower than the high-dose group and in the 1 to 5 ng/mL range.

All subjects had portal hypertension as determined by HVPG at baseline (mean 19.7 mmHg, range 9-29 mmHg). Throughout the study, the high-dose group experienced an increase in HVPG. The increase in HVPG was apparent in the first 90 minutes following the administration of ambrisentan, with a further increase after 14 days of treatment. Unlike the high-dose group, the low-dose group experienced a decrease in portal pressure as determined by HVPG. An initial decrease in HVPG was apparent at 90 minutes post-administration in the low-dose group, and the reduction in HVPG was even larger at day 14 when compared to day 1 (Table 2).

TABLE 2

Change in Hepatic Venous Pressure Gradient (HVPG) from baseline following the administration of ambrisentan for 14 days at two different doses. Results expressed as percent change from baseline and standard error of the mean in parentheses: mean (SE).

| Dose Group | N | Day 1 Baseline (0 H) | Day 1 90 m | Day 14 Trough (0 H) | Day 14 90 m |
|---|---|---|---|---|---|
| 10/14 µg | 4 | — | −6.4% (7.4%) | −9.2% (12.9%) | −14.1% (9.2%) |
| 50/200 µg | 4 | — | 4.8% (4.1%) | 9.2% (12.8%) | 11.7% (14.1%) |

Figure 1:
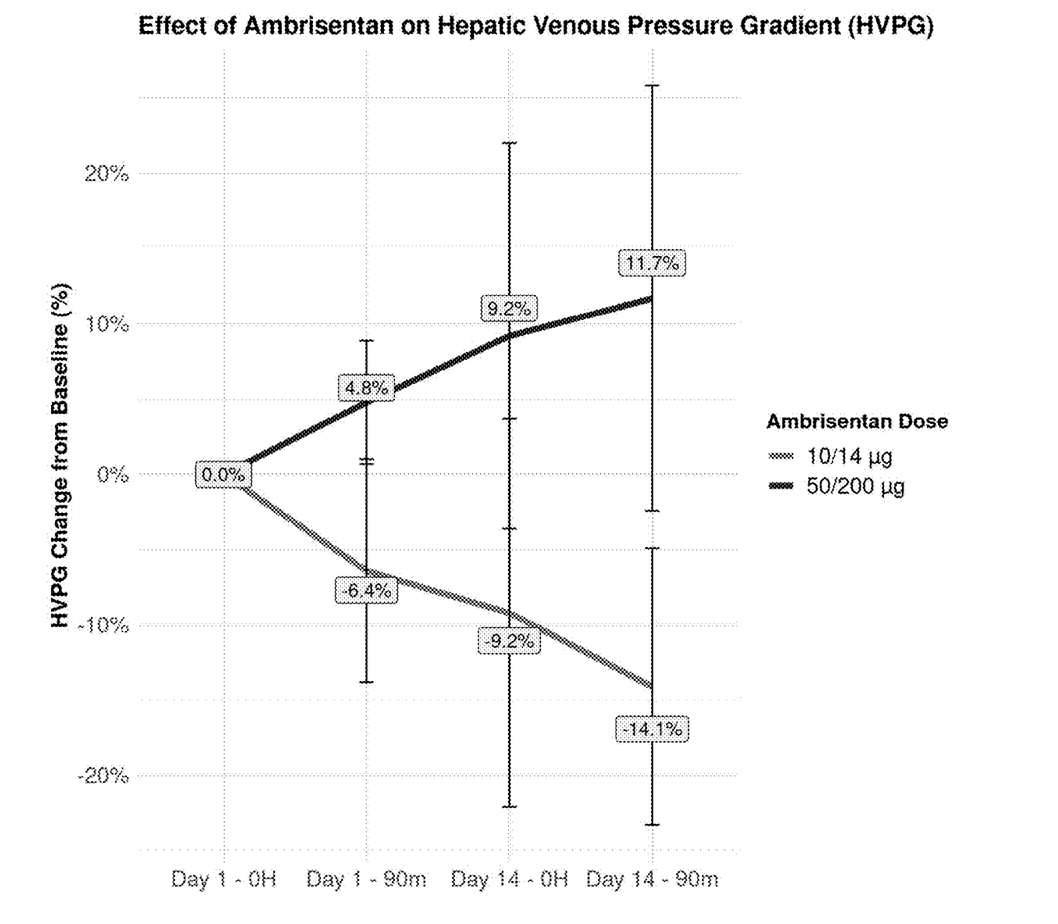
FIG. 1 shows the effect of ambrisentan on Hepatic Venous Pressure Gradient (HVPG) from baseline administration of ambrisentan for 14 days at two different doses.

The results are also presented in FIG. 1. These results indicate that the effect of ambrisentan in reducing portal pressure is dependent on the concentration of ambrisentan in blood plasma. Ambrisentan concentrations in plasma below 10 ng/mL are effective in reducing portal pressure in patients with portal hypertension. Concentrations of ambrisentan in plasma above 10 ng/mL result in the opposite effect, i.e. an increase in portal pressure.

The references referred to in the description are shown below and form part of the description.

[1] G. Baffy, "Origins of Portal Hypertension in Nonalcoholic Fatty Liver Disease," *Dig. Dis. Sci.*, vol. 63, no. 3, pp. 563-576, 2018.

[2] A. H. Moreno, A. R. Burchell, L. M. Rousselot, W. F. Panke, F. Slafsky, and J. H. Burke, "Portal blood flow in cirrhosis of the liver," *J Clin Invest*, vol. 46, no. 3, pp. 436-445, 1967.

[3] J. Bosch, J. G. Abraldes, A. Berzigotti, and J. C. Garcia-Pagan, "The clinical use of HVPG measurements in chronic liver disease," *Nat. Rev. Gastroenterol. Hepatol.*, vol. 6, no. 10, pp. 573-582, 2009.

[4] K. Moore, "Endothelin and vascular function in liver disease.," *Gut*, vol. 53, no. 2, pp. 159-61, February 2004.

[5] K. Moore, J. Wendon, M. Frazer, J. Karani, R. Williams, and K. Badr, "Plasma endothelin immunoreactivity in liver disease and the hepatorenal syndrome.," *N. Engl. J. Med., vol.* 327, no. 25, pp. 1774-8, December 1992.

[6] T. Okamoto et al., "Antifibrotic effects of ambrisentan, an endothelin-A receptor antagonist, in a non-alcoholic steatohepatitis mouse model," *World J. Hepatol.*, vol. 8, no. 22, pp. 933-941, 2016.

[7] K. Pitts, "Endothelin receptor antagonism in portal hypertension," *Expert Opin. Investig. Drugs*, vol. 18, no. 2, pp. 135-142, 2009.

[8] D. Tripathi, G. Therapondos, J. W. Ferguson, D. E. Newby, D. J. Webb, and P. C. Hayes, "Endothelin-1 contributes to maintenance of systemic but not portal haemodynamics in patients with early cirrhosis: a randomised controlled trial.," *Gut*, vol. 55, no. 9, pp. 1290-5, 2006.

[9] A. Zipprich, E. Schenkel, M. Winkler, and C. Ripoll, "Selective Endothelin-A-Blocker decrease portal pressure in patients with cirrhosis. A feasibility study combining the local intraarterial and systemic administration," *Z. Gastroenterol.*, vol. 54, no. 12, pp. 1343-1404, December 2016.

[10] M. Halank et al., "Ambrisentan improves exercise capacity and symptoms in patients with portopulmonary hypertension.," *Z. Gastroenterol.*, vol. 49, no. 9, pp. 1258-62, September 2011.

[11] L. Savale et al., "Efficacy, safety and pharmacokinetics of bosentan in portopulmonary hypertension," *Eur. Respir. J.*, vol. 41, no. 1, pp. 96-103, 2013.

[12] M. M. Hoeper et al., "Experience with inhaled iloprost and bosentan in portopulmonary hypertension.," *Eur. Respir. J.*, vol. 30, no. 6, pp. 1096-102, December 2007.

[13] C. M. Uhler, I. Graziadei, H. Vogelsinger, S. Desole, K. Cima, and W. Vogel, "Successful treatment of portopulmonary hypertension with the selective endothelin receptor antagonist Sitaxentan.," *Wien. Klin. Wochenschr.*, vol. 123, no. 7-8, pp. 248-52, April 2011.

[14] H. Muraoka et al., "Secure Combination Therapy With Low-Dose Bosentan and Ambrisentan to Treat Portopulmonary Hypertension Minimizing Each Adverse Effect.," *Int. Heart J.*, vol. 56, no. 4, pp. 471-3, 2015.

[15] Y. Yamashita et al., "Hemodynamic effects of ambrisentan-tadalafil combination therapy on progressive portopulmonary hypertension.," *World J. Hepatol.*, vol. 6, no. 11, pp. 825-9, November 2014.

[16] L. Hinterhuber, I. W. Graziadei, C. M. Uhler, W. Jaschke, and W. Vogel, "Endothelin-receptor antagonist treatment of portopulmonary hypertension," *Clin. Gastroenterol. Hepatol.*, vol. 2, no. 11, pp. 1039-1042, 2004.

[17] O. Sitbon et al., "Macitentan for the treatment of portopulmonary hypertension (PORTICO): a multicentre, randomised, double-blind, placebo-controlled, phase 4 trial," *Lancet Respir. Med.*, vol. 7, no. 7, pp. 594-604, 2019.

[18] R. Cartin-Ceba and M. J. Krowka, "Safety and efficacy of ambrisentan for the therapy of portopulmonary hypertension (POPH)," *Hepatology*, vol. 50, no. 4, pp. 348A-349A, 2009.

[19] R. Cartin-Ceba, K. Swanson, V. Iyer, R. H. Wiesner, and M. J. Krowka, "Safety and efficacy of ambrisentan for the treatment of portopulmonary hypertension," *Chest*, vol. 139, no. 1, pp. 109-114, January 2011.

[20] R. Cartin-Ceba and M. J. Krowka, "Portopulmonary hypertension.," *Clin. Liver Dis.*, vol. 18, no. 2, pp. 421-38, May 2014.

The invention claimed is:

1. A method for treating a subject suffering from portal hypertension comprising administering ambrisentan wherein an effective amount of ambrisentan is administered to the subject, wherein ambrisentan is administered to a treated subject such that the plasma levels of ambrisentan are maintained below 10 ng/ml.

2. A method for treating a subject suffering from portal hypertension associated with cirrhosis comprising administering ambrisentan wherein an effective amount of ambrisentan is administered to the subject, wherein ambrisentan is administered to a treated subject such that the plasma levels of ambrisentan are maintained below 10 ng/ml.

* * * * *